United States Patent [19]

Liberati

[11] Patent Number: 5,042,506
[45] Date of Patent: Aug. 27, 1991

[54] ANTISNORING TRAINING DEVICE

[76] Inventor: Salvator P. Liberati, 7606 McHenry Avenue, Crystal Lake, Ill. 60014

[21] Appl. No.: 509,719

[22] Filed: Apr. 16, 1990

Related U.S. Application Data

[63] Continuation-in-part of Ser. No. 431,015, Nov. 2, 1989, abandoned.

[51] Int. Cl.$^5$ ............................................. A61F 5/56
[52] U.S. Cl. ................................. 128/848; 128/859
[58] Field of Search ................. 128/848, 861, 862, 859

[56] References Cited

U.S. PATENT DOCUMENTS

| | | | |
|---|---|---|---|
| 1,146,264 | 7/1915 | Kelly | 128/861 X |
| 1,302,004 | 4/1919 | Brown | 128/861 |
| 2,694,397 | 11/1954 | Herms | 128/861 |
| 3,073,300 | 1/1963 | Berghash | 128/862 |
| 3,082,765 | 3/1963 | Helmer | 128/861 X |
| 3,207,153 | 9/1965 | Goldstein | 128/862 |
| 3,319,626 | 5/1967 | Lindsay | 128/861 |
| 3,496,936 | 2/1970 | Gores | 128/861 |
| 3,768,465 | 10/1973 | Helmer | 128/862 |
| 4,185,817 | 1/1980 | Peterson | 128/861 X |
| 4,944,947 | 7/1990 | Newman | 128/861 X |

FOREIGN PATENT DOCUMENTS 312368  4/1989  European Pat. Off. ............ 128/848

Primary Examiner—Robert A. Hafer
Assistant Examiner—Kevin G. Rooney
Attorney, Agent, or Firm—Mathew R. P. Perrone, Jr.

[57] ABSTRACT

An antisnoring device is found in a U-shaped, wedge-like intraoral training appliance that separates the teeth, provides additional intraoral space for the tongue and retrains as it tones up the muscles of degletition and mastication while the user is in a sleep induced state. Thereby resulting in a more open airway space facilitating the improvement of snoring, of obstructive sleep apnea and nocturnal occlusal trauma.

19 Claims, 1 Drawing Sheet

ANTISNORING TRAINING DEVICE

CROSS REFERENCE TO RELATED APPLICATION

This application is a continuation in part of U.S. patent application Ser. No. 07/431,015 filed by the same inventor on Nov. 2, 1989 now abandoned.

This invention relates to an antisnoring device and more particularly to an intraoral muscle training appliance for the prevention of snoring, obstruction sleep apnea, and nocturnal trauma.

BACKGROUND OF THE INVENTION

Numerous dental appliances for snore reduction, improving obstructive sleep apnea, and reducing trauma to the dentition during sleep are known in the art. Equally numerous is a variety of design differences that share common characteristics in form and function, which fail to properly correct the problems. The present invention improves and corrects these problems more efficiently.

These former various devices mechanically restrict the movement of the hard and soft tissue of the oral cavity. They also require a protrusion of the jaw, to increase intraoral space essential to accomodate the tongue and to increase the oral pharyngeal airway space. In addition, a common characteristic of the prior art devices is infringement upon the intraoral space with a variety of custom fitted palatal plates, clasps, arch wires tongue retracters, uvala telescope and incisal guides in addition to covering the teeth. Furthermore, a common problem with all of these devices is clearly that they are very discomforting to the user.

These prior devices are restrictive to soft and hard tissues of the oral cavity. The stated discomfort is inconsistent with the sleep induced state of muscle physiology and the anatomical repositioning of the jaw. Snoring, obstructive sleep apnea, and occlusal trauma are viewed as one entity for the purpose of this invention, that can best be addressed through a retraining and toning of the related muscle groups, increasing the intermaxillary space, and by not encroaching upon the available oral cavity space. However, no known device addresses these problems.

SUMMARY OF THE INVENTION

Therefore, among the many objectives of this invention is to provide a device capable of treating the triad of conditions previously described and referred to as one entity by use of an intraoral training wedge.

A further object of this invention is to provide a device, which permits the sleep induced relaxation of the muscles of mastication to anatomically reposition the retrusion of the jaw.

A still further object of the invention is to provide a device, which recaptures and provides additional essential intermaxillary space to accommodate the tongue while avoiding encroachment of that space.

Yet a further object of the invention is to provide a device which absorbs, dissipates and evenly distributes nocturnal functional and parafunctional occlusal trauma.

Also a further object of this invention is to provide a device, which assists the muscle toning and retraining of the oralpharyngeal and related muscles during the functional and parafunctional jaw movements while in the sleep induced state.

Another object of this invention is to provide a device to promote a natural adhesion and suction for the tongue on the roof of the mouth.

These and other objects of this invention are met by providing an intraoral, anti-snoring device having the general shape of a U-shaped wedge with its thickest portion centrally located therein and further provided with surface slots to provide for passage of saliva.

BRIEF DESCRIPTION OF THE DRAWINGS

Throughout the Figures of the drawing, where the same part appears in more than one Figure of the drawing, the same number is applied thereto.

DESCRIPTION OF THE PREFERRED EMBODIMENTS

The anti-snoring device of this invention is in the form of intraoral, wedge-like, training appliance to serve three purposes. The training appliance inhibits snoring, improves obstructive sleep apnea, and minimizes the harmful effects of occlusal trauma.

The present invention is an anti-snoring device that is nonrestrictive to soft and hard tissues of the oral cavity. It is consistent with the sleep induced state of muscle physiology and the anatomical repositioning of the jaw. It is viewed that snoring, obstructive sleep apnea, and occlusal trauma are entities that can best be addressed through a retraining and toning of the related muscle groups, while increasing the intermaxillary space and not encroaching upon the available oral cavity space.

Figure 1:
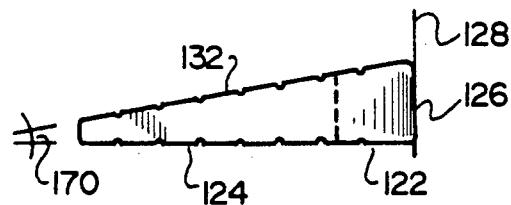
FIG. 1 depicts a side, plan view of the anti-snoring device 100.

Referring now to FIG. 1, the anti-snoring device 100, shown when in use, is wedged between the teeth 112 of head 110. The anti-snoring device 100 is symmetrically U-shaped in form having an arcuate base portion 120, which forms the thickest portion of device 100. Lower portion 122 of device 100 is included in a lower plane 124. Outer edge 126 of device 100 includes an arcuate plane 128 which is substantially perpendicular to lower plane 124. Upper portion 130 of device 100 is included in upper plane 132. Upper plane 132 lacks perpendicularity with arcuate plane 128 and intersects lower plane 124 adjacent posterior end 140.

Lower plane 124, upper plane 132, and arcuate plane 128 form no part of device 100 but are defined to explain the shape of device 100, which provides a major portion of the inventive concept, with device 100 as a free floating wedge.

Figure 2:
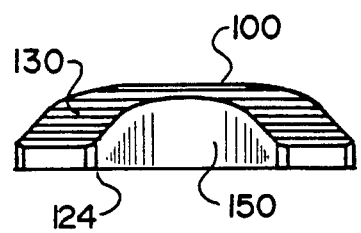
FIG. 2 depicts a rear, perspective view of the anti-snoring device 100.

FIG. 2 depicts a posterior view of the anti-snoring device 100 and a posterior wall 150 of its arcuate base portion 120. Posterior wall 150 is oppositely disposed from outer edge 126.

Figure 3:
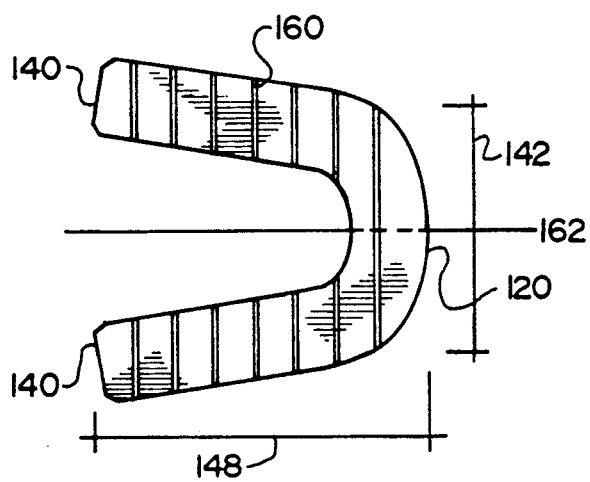
FIG. 3 depicts a top, plan view of the anti-snoring device 100.

Referring now to FIG. 3, a top view of FIG. 1 is depicted. The upper portion 130 and the lower portion 122 may each be striated with at least one channel 160 that allows free flow of saliva around the device 100 and helps stabilize the teeth 112. Such striation can be jointly or severally in the upper portion 130 or the lower portion 122. As shown, each of channel 160 is parallel to the other and basically perpendicular to an imaginary plane of symmetry 162 for device 100. Preferably, there are at least four of the channels 160 in both the upper portion 130 and the lower portion 122.

Figure 4:
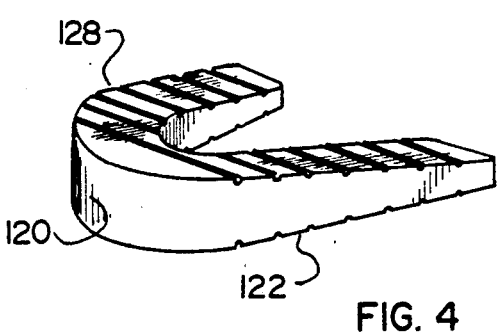
FIG. 4 depicts a side, top, perspective view of the anti-snoring device 100.

Referring now to FIG. 4, a reverse, perspective view of FIG. 1 is depicted. In this perspective view, it is revealed that the posterior wall 150 of the device 100 is placed in the back of the mouth 114 with lower portion 122 resting on the lower teeth 112 and upper portion 130 separating the upper teeth 112 from the lower. Channels 160 allow the free flow of saliva and provide grooves for stabilizing the teeth 112 as well. Again let it be noted that the upper anterior teeth 112 need not be in contact with arcuate base portion 120 during use.

Figure 5:
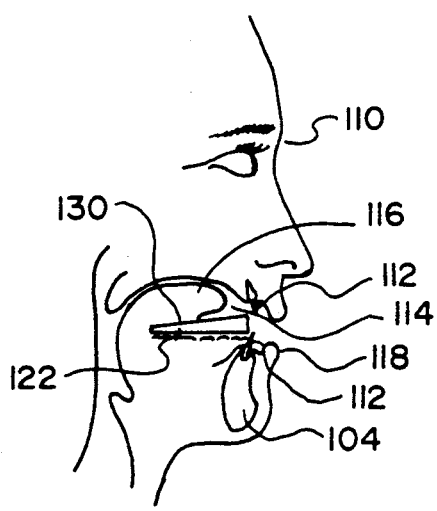
FIG. 5 depicts a partial cross-section view of a human head 110 as it might typically appear with anti-snoring device 100 in place.

FIG. 5 depicts a cross-section of device 100 viewed as it might typically be used in an open retruded mandible 104. FIG. 5 further depicts a sagital view of the device 100 as typically used. The wearer is instructed to place the anti-snoring device 100 on his lower teeth 112 as far back in the mouth 114 as is comfortable; to place the tip 116 of the tongue on the roof of the mouth 114 resting the teeth 112 on the device 100; with lips 118 closed and breathing through the nose, and swallowing comfortably. While the wearer sleeps, the mandible 104 relaxes in a retruded mandibular position. As swallowing occurs, the muscles are retrained to function from the relaxed sleep induced retruded position which increases the oral pharyngeal airway space, produces suction of the tongue against the roof of the mouth 114, and tones and retrains the muscles related thereto simultaneously.

Referring now to FIG. 5, the anti-snoring device 100, shown when in use shows posterior end 140 placed as far back into the mouth 114 as is possible staying within the comfort tolerance of the wearer. Posterior end 140 is the thinnest portion of device 100. Anterior end, which is oppositely disposed from posterior end 140, is at the vertex of outer edge 126 and is the thickest portion of anti-snoring device 100 and is adjacent arcuate base portion 120.

The lower portion 122 lies on the teeth 112 of the lower arch or mandible 104 and can be adjusted forward or backward into the mouth 114. This adjustment increases or decreases the amount of intermaxillary distance and oral pharyngeal muscle tone and training.

An angle 170 between lower plane 124 and upper plane 132 is preferably in the range of two (2°) degrees to fifteen (15°) degrees. More preferably, angle 170 is in the range of four (4°) degrees to thirteen (13°) degrees. Most preferably, angle 170 is in the range of about six (6°) degrees to about nine (9°) degrees.

The various sizes of device 100 can easily be determined on an individual basis and mouth size. A framework of sizes as set forth below provides a basis for determining an appropriate size. Three sizes—small, medium, and large can usually serve most people.

Channels 160 must be of sufficient depth to permit flow of saliva, and have a diameter of up to five millimeters. More preferably, channels 160 have a diameter of 0.5 millimeter to 4.0 millimeters. Most preferably, channels 160 have a diameter of about 1.0 millimeter to about 2.0 millimeters.

Device 100 is varied in size to fit a mouth. Posterior end 140, the thinnest portion of device 100, is preferably 1.0 millimeter to 11 millimeters thick. More preferably, posterior end 140 is preferably 2.0 millimeters to 9.0 millimeters thick. Most preferably, posterior end 140 is preferably about 3.0 millimeters to about 7.0 millimeters thick.

Lower portion 122 and upper portion 130 are preferably 5.0 millimeters to 15 millimeters wide. More preferably, lower portion 122 and upper portion 130 are preferably 6.0 millimeters to 14 millimeters wide. Most preferably, lower portion 122 and upper portion 130 are preferably about 7.0 millimeters to about 13.0 millimeters wide.

The overall length 148 of device 100 from posterior end 140 to arcuate base portion 120 (anterior end) for a medium sized device 100 is about 10 millimeters to about 35 millimeters. More preferably, the overall length 148 is about 15 millimeters to about 30 millimeters. Most preferably, the overall length 148 is about 20 millimeters to about 25 millimeters. The length 148 of a small-sized device 100 is reduced to about 5 millimeters less than a medium sized device 100, while the length 148 of a large-sized device 100 is increased to about 5 millimeters more than a medium sized device 100.

The overall width 142 of device 100 for a medium sized device 100 is about 20 millimeters to about 50 millimeters. More preferably, the overall width 142 is about 25 millimeters to about 45 millimeters. Most preferably, the overall width 142 is about 30 millimeters to about 40 millimeters. The width 142 of a small-sized device 100 is reduced to about 5 millimeters less than a medium sized device 100, while the width 142 of a large-sized device 100 is increased to about 5 millimeters more than a medium sized device 100.

Device about 100 may be made of any suitable, pharmaceutically acceptable, thermoplastic material having the resilient durability required. The material must be firm, but not impenetrable.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of the invention of this application can become clear to a person having ordinary skill in this particular art. Such modifications are clearly covered by this disclosure.

What is claimed and sought to be protected by Letters Patent of the United States is:

1. An anti-snoring device for use as an intraoral muscle training appliance in a mouth of a person, said anti-snoring device having a U-shaped, wedge shape to separate upper teeth from lower teeth in said mouth and rest on said lower teeth, to provide additional intraoral space for the tongue and retrain while toning up the muscles of degletition and mastication while during sleep, wherein:
   (a) said anti-snoring device has a lower portion substantially containable within an imaginary lower plane;
   (b) said anti-snoring device has an arcuate base portion substantially contained within an imaginary arcuate plane;
   (c) said anti-snoring device has a upper portion substantially contained within an imaginary upper plane;

(d) said anti-snoring device has a posterior end oppositely disposed from said arcuate base portion;
(e) said imaginary upper plane intersects said imaginary lower plane adjacent said posterior end;
(f) said imaginary arcuate plane is substantially perpendicular to said imaginary lower plane;
(g) said anti-snoring device includes at least one channel to permit saliva flow around said anti-snoring device;
(h) said arcuate base portion includes a posterior wall and an outer edge;
(i) said posterior wall is oppositely disposed from said outer edge;
(j) said imaginary arcuate plane contains said outer edge;
(k) said lower portion is striated with said at least one channel to allow free flow of saliva around said anti-snoring device; and
(l) said upper portion is striated with said at least one channel to allow free flow of saliva around said anti-snoring device.

2. The anti-snoring device of claim 1, wherein said at least one channel is substantially perpendicular to an imaginary plane of symmetry for said anti-snoring device.

3. The anti-snoring device of claim 2, wherein:
(a) said anti-snoring device includes a posterior end placeable in the back of a mouth;
(b) said lower portion rests on the lower teeth in said mouth; and
(c) said upper portion separates the upper teeth in said mouth from said lower teeth.

4. The anti-snoring device of claim 3, wherein:
(a) said posterior end is oppositely disposed from an anterior end;
(b) said anterior end is a thickest portion of said anti-snoring device; and
(c) said anterior end includes said arcuate base portion.

5. The anti-snoring device of claim 4, wherein:
(a) said imaginary upper plane intersects said imaginary lower plane at angle of about two degrees to about fifteen degrees; and
(b) said at least one channel has a diameter of up to about five millimeters.

6. The anti-snoring device of claim 5, wherein:
(a) said posterior end is the thinnest portion of said anti-snoring device and is about 1.0 millimeter to about 11 millimeters thick; and
(b) said lower portion and said upper portion are about 5.0 millimeters to about 15.0 millimeters thick.

7. The anti-snoring device of claim 6, wherein:
(a) said imaginary upper plane intersects said imaginary lower plane at angle of about four degrees to about thirteen degrees;
(b) said at least one channel has a diameter of about 0.5 millimeter to about four millimeters;
(c) said posterior end is the thinnest portion of said anti-snoring device and is about two millimeters to about nine millimeters thick; and
(d) said lower portion and said upper portion are about six millimeters to about fourteen millimeters thick.

8. The anti-snoring device of claim 7, wherein:
(a) said imaginary upper plane intersects said imaginary lower plane at angle of about six degrees to about nine degrees;
(b) said at least one channel has a diameter of about one millimeter to about two millimeters;
(c) said posterior end is the thinnest portion of said anti-snoring device and is about three millimeters to about seven millimeters thick; and
(d) said lower portion and said upper portion are about seven millimeters to about thirteen millimeters thick.

9. The anti-snoring device of claim 8, wherein:
(a) an overall length of said device form said posterior end to said anterior end about 10 millimeters to about 35 millimeters for a medium sized version of said device; and
(b) an overall width of said device measured along a perpendicular to said overall length is about 20 millimeters to about 50 millimeters for a medium sized version of said device.

10. The anti-snoring device of claim 9, wherein:
(a) said overall length of said device form said posterior end to said anterior end about 15 millimeters to about 30 millimeters for said medium sized version of said device; and
(b) said overall width of said device measured along a perpendicular to said overall length is about 25 millimeters to about 45 millimeters for said medium sized version of said device.

11. The anti-snoring device of claim 10, wherein:
(a) said overall length of said device form said posterior end to said anterior end about 20 millimeters to about 25 millimeters for said medium sized version of said device; and
(b) said overall width of said device measured along a perpendicular to said overall length is about 30 millimeters to about 40 millimeters for said medium sized version of said device.

12. The anti-snoring device of claim 9, wherein a large size of said device is about 5 millimeters larger than said overall length and said overall width.

13. The anti-snoring device of claim 9, wherein a small size of said device is about 5 millimeters less than than said overall length and said overall width.

14. An anti-snoring device for use as an intraoral muscle training appliance in a mouth of a person, said anti-snoring device consisting essentially of a U-shaped, wedge shape to separate upper teeth from lower teeth in said mouth and rest on said lower teeth, to provide additional intraoral space for the tongue and retain while toning up the muscles of deglition and mastication while during sleep, wherein:
(a) said anti-snoring device has a lower portion substantially containable within an imaginary lower plane;
(b) said anti-snoring device has an arcuate base portion substantially contained within an imaginary arcuate plane;
(c) said anti-snoring device has an upper portion substantially contained within an imaginary upper plane;
(d) said anti-snoring device has a posterior end oppositely disposed from said arcuate base portion;
(e) said imaginary upper plane intersects said imaginary lower plane adjacent said posterior end;
(f) said imaginary arcuate plane is substantially perpendicular to said imaginary lower plane;
(g) said arcuate base portion includes a posterior wall and an outer edge;
(h) said posterior wall is oppositely disposed from said outer edge;

(i) said imaginary arcuate plane contains said outer edge;

(j) said upper portion is striated with at least one channel to allow free flow of saliva around said anti-snoring device;

(k) said lower portion is striated with at least one channel to allow free flow of saliva around said anti-snoring device;

(l) said at least one channel is substantially perpendicular to an imaginary plane of symmetry for said anti-snoring device;

(m) said anti-snoring device includes a posterior end placeable in the back of a mouth;

(n) said lower portion rests on said lower teeth in said mouth; and (o) said upper portion receives said upper teeth;

(p) said anti-snoring device separates said upper teeth in said mouth from said lower teeth.

15. The anti-snoring device of claim 14, wherein:
(a) said posterior end is oppositely disposed from an anterior end;
(b) said anterior end is a thickest portion of said anti-snoring device;
(c) said anterior end is adjacent said arcuate base portion;
(d) said imaginary upper plane intersects said imaginary lower plane at angle of about two degrees to about fifteen degrees;
(e) said at least one channel has a diameter of up to about five millimeters;
(f) said posterior end is the thinnest portion of said anti-snoring device and is about 1.0 millimeter to about 11 millimeters thick;
(g) said lower portion and said upper portion are about 5.0 millimeters to about 15.0 millimeters thick.

16. The anti-snoring device of claim 15, wherein:
(a) said imaginary upper plane intersects said imaginary lower plane at angle of about four degrees to about thirteen degrees;
(b) said at least one channel has a diameter of about 0.5 millimeter to about four millimeters;
(c) said posterior end is the thinnest portion of said anti-snoring device and is about two millimeters to about nine millimeters thick;
(d) said lower portion and said upper portion are about six millimeters to about fourteen millimeters thick.

17. The anti-snoring device of claim 16, wherein:
(a) said imaginary upper plane intersects said imaginary lower plane at angle of about six degrees to about nine degrees;
(b) said at least one channel has a diameter of about one millimeter to about two millimeters;
(c) said posterior end is the thinnest portion of said anti-snoring device and is about three millimeters to about seven millimeters thick;
(d) said lower portion and said upper portion are about seven millimeters to about thirteen millimeters thick.

18. The anti-snoring device of claim 17, wherein:
(a) an overall length of said device form said posterior end to said anterior end about 10 millimeters to about 35 millimeters for a medium sized version of said device; and
(b) an overall width of said device measured along a perpendicular to said overall length is about 20 millimeters to about 50 millimeters for a medium sized version of said device.

19. A method for minimizing snoring by inserting an anti-snoring device in a mouth of a person during sleeping time, retraining and toning muscles, said anti-snoring device having a U-shaped, wedge shape to separate upper teeth from lower teeth in said mouth and rest on said lower teeth, to provide additional intraoral space for the tongue and retrain while toning up the muscles of degletition and mastication while during sleep, wherein:
(a) said anti-snoring device has a lower portion substantially contained within an imaginary lower plane;
(b) said anti-snoring device has an arcuate base portion substantially contained within an imaginary arcuate plane;
(c) said anti-snoring device has a upper portion substantially contained within an imaginary upper plane;
(d) said anti-snoring device has a posterior end oppositely disposed from said arcuate base portion;
(e) said imaginary upper plane intersects said imaginary lower plane adjacent said posterior end;
(f) said imaginary arcuate plane is substantially perpendicular to said imaginary lower plane;
(g) said arcuate base portion includes a posterior wall and an outer edge;
(h) said posterior wall is oppositely disposed from said outer edge;
(i) said imaginary arcuate plane contains said outer edge;
(j) said upper portion is striated with at least one channel to allow free flow of saliva around said anti-snoring device;
(k) said lower portion is striated with at least one channel to allow free flow of saliva around said anti-snoring device;
(l) said at least one channel is substantially perpendicular to an imaginary plane of symmetry for said anti-snoring device;
(m) said anti-snoring device includes a posterior end placeable in the back of a mouth;
(n) said lower portion rests on the lower teeth in said mouth; and
(o) said upper portion receives the upper teeth in said mouth from said lower teeth.

* * * * *